United States Patent [19]

Morishima et al.

[11] Patent Number: 5,348,733
[45] Date of Patent: Sep. 20, 1994

[54] ORAL COMPOSITION

[75] Inventors: Seiji Morishima, Odawara; Miwako Oka, Yokohama; Yamazaki Yoji, Hiratsuka, all of Japan

[73] Assignee: Lion Corporation, Tokyo, Japan

[21] Appl. No.: 971,593

[22] Filed: Nov. 5, 1992

[30] Foreign Application Priority Data

Nov. 6, 1991 [JP] Japan .................. 3-318534

[51] Int. Cl.$^5$ .................. A61K 7/16; A61K 7/18
[52] U.S. Cl. .................. 424/52; 424/49
[58] Field of Search .................. 424/49–58

[56] References Cited

U.S. PATENT DOCUMENTS

| | | | |
|---|---|---|---|
| 4,894,220 | 1/1990 | Nabi et al. | 424/52 |
| 5,015,466 | 5/1991 | Parran et al. | 424/52 |
| 5,015,467 | 5/1991 | Smitherman | 424/52 |
| 5,032,386 | 7/1991 | Gaffar et al. | 424/49 |
| 5,037,635 | 8/1991 | Nabi et al. | 424/52 |
| 5,037,637 | 8/1991 | Gaffar et al. | 424/52 |
| 5,043,154 | 8/1991 | Gaffar et al. | 424/52 |
| 5,080,887 | 1/1992 | Gaffar et al. | 424/52 |
| 5,094,845 | 3/1992 | Vlock | 424/52 |
| 5,096,702 | 3/1992 | Rolla et al. | 424/52 |
| 5,108,734 | 4/1992 | Colodney et al. | 424/49 |
| 5,156,835 | 10/1992 | Nabi et al. | 424/52 |
| 5,165,914 | 11/1992 | Vlock | 424/52 |
| 5,167,951 | 12/1992 | Gaffar et al. | 424/49 |
| 5,180,578 | 1/1993 | Gaffar et al. | 424/52 |
| 5,192,533 | 3/1993 | Elliott et al. | 424/54 |
| 5,234,688 | 8/1993 | Gaffar | 424/401 |
| 5,240,696 | 8/1993 | Van Der Oudera | 424/99 |
| 5,240,697 | 8/1993 | Norfleet et al. | 424/52 |

FOREIGN PATENT DOCUMENTS

| | | |
|---|---|---|
| 60-239409 | 11/1985 | Japan . |
| 62-89614 | 4/1987 | Japan . |
| 62-126116 | 6/1987 | Japan . |
| 6410489 | 2/1989 | Japan . |
| 2-11511 | 1/1990 | Japan . |
| 3-5416 | 1/1991 | Japan . |
| 3127719 | 5/1991 | Japan . |

*Primary Examiner*—Shep K. Rose

[57] ABSTRACT

An oral composition comprises triclosan, an alkyl sulfate and a water-soluble tin salt, whereby triclosan can be stably formulated to exert its effect.

10 Claims, No Drawings

ORAL COMPOSITION

BACKGROUND OF THE INVENTION

1. Industrial Field

The present invention relates to an oral composition which comprises triclosan (2,4,4'-trichloro-2'-hydroxydiphenyl ether) and more particularly, to an oral composition wherein the lowering in activity of triclosan by surface active agents can be prevented and the germicidal activity of triclosan is shown to a satisfactory extent.

2. Prior Art

It is known that oral compositions such as dentifrice which comprise triclosan as an effective ingredient can inhibit the formation of dental plaque because of the intense germicidal action of triclosan. In fact, there has been proposed incorporation, in oral compositions comprising triclosan, of zinc salts (Japanese Laid-open Patent Application Nos. 60-239409 and 3-127719, and Japanese Patent Publication No. 64-10489), copper compounds (Japanese Laid-open Patent Application No. 62-89614), polyethylene glycol (Japanese Laid-open Patent Application No. 62-126116), and the like.

However, when triclosan and a surface active agent such as alkyl sulfates ordinarily used as a foaming agent are used in combination, the germicidal activity is considerably lowered, with the problem that the effect of triclosan is not shown satisfactorily. In order to solve this problem, the present applicant already proposed the formulation of phenolic compounds (Japanese Laid-open Patent Application No. 2-11511) or water-soluble calcium salts (Japanese Laid-open Patent Application No. 3-5416) in an oral composition which comprises triclosan and a surface active agent. More effective measures for the dissolution are desirable.

It is essential to add a surface active agent to an oral composition such as dentifrice in order to make foams on use and to improve the feel in use. In particular, alkyl sulfates which are anionic surface active agents are most widely employed for this purpose. However, it presents a serious problem that triclosan which is added to oral compositions is impeded in activity by means of surface active agents. There is a demand of inhibiting the lowering in the activity of triclosan by surface active agents.

SUMMARY OF THE INVENTION

An object of the present invention is to provide an oral composition containing triclosan in combination with an alkyl sulfate in which triclosan can be stably formulated to exert its effect, thereby preventing the formation of dental plaque and the occurrence of gingivitis.

We made intensive studies and, as a result, found that when a water-soluble tin salt is added to an oral composition which comprises triclosan and an alkyl sulfate surface active agent, the triclosan can be stably formulated in the composition comprising the alkyl sulfate surface active agent whereby the germicidal activity of triclosan can be effectively inhibited from lowering and shows its intense germicidal activity effectively.

As will become apparent from experiments described later, such an effect as set forth above is not produced when sparingly soluble or insoluble tin salts such as stannous pyrophosphate are added to oral compositions which comprise both triclosan and alkyl sulfates, but is developed only when water-soluble tin salts are added. Moreover, any stable composition is not obtained when water-soluble tin salts are added to triclosan and alkyl ether sulfates. Unexpectedly, we have found that when trichlosan, alkyl sulfates and water-soluble salts are used in combination, triclosan is stabilized. The invention is accomplished based on the finding that the stabilization of trichlosan results from a combination of these three ingredients.

It is known to formulate either alkyl sulfate surface active agents or water-soluble tin salts to triclosan-containing oral compositions (Japanese Laid-open Patent Application Nos. 62-89614 and 3-127719). Nevertheless, it is our finding that when triclosan, an alkyl sulfate surface active agent an a water-soluble tin salt are used in combination, a significant synergistic effect is obtained.

Therefore, according to the present invention, there is provided an oral composition comprising triclosan (2,4,4'-trichloro-2'-hydroxydiphenyl ether), an alkyl sulfate and a water-soluble tin salt.

DETAILED DESCRIPTION OF THE INVENTION

The oral composition of the invention may be used in the form of dentifrices such as toothpastes, toothpowders and liquid dentifrices, mouthwashes, gingiva-massage creams, liquid or paste regional ointments, troches, chewing gums and the like. The composition comprises, in combination, triclosan, an alkyl sulfate surface active agent and a water-soluble tin salt.

The amount of triclosan is not critical and is generally in the range of 0.001 to 1.0% by weight, preferably 0.01 to 0.5% by weight of the total weight of the oral composition.

The alkyl sulfate used as the surface active agent is one whose carbon chain has 8 to 18 carbon atoms, preferably 10 to 14 carbon atoms. Specific examples of the alkyl sulfate surface active agent include sodium lauryl sulfate, sodium myristyl sulfate and the like.

The amount of the alkyl sulfate is not critical and generally in the range of 0.01 to 10% by weight, preferably 0.1 to 5% by weight of the total weight of the composition.

The water-soluble tin salts may be either inorganic or organic so long as they can be formulated from the pharmaceutical standpoint. Specific examples include stannous fluoride, stannous chloride, stannous fluoride chloride, stannous acetate, stannous sulfate, stannous tartrate, stannous gluconate, stannous citrate and the like. Of these, stannous fluoride stannous chloride and stannous gluconate are preferred.

The amount of the water-soluble tin salt is not critical and is generally in the range of 0.01 to 10% by weight, preferably 0.1 to 2% by weight of the total weight of the composition. If the amount is less than 0.01% by weight, the lowering in the activity of triclosan in the composition may not be prevented. Over 5% by weight, the feel of the composition may be impeded.

Depending on the purpose and the type of composition, the oral composition of the invention may further comprise, aside from the above-stated ingredients, abrasives, binders, humectants, flavors and other effective ingredients in amounts not impeding the germicidal effect of triclosan.

Examples of the abrasive include calcium hydrogen phosphate dihydrate, calcium carbonate, calcium pyrophosphate, calcium sulfate, insoluble sodium metaphosphate, silicic anhydride, hydrous silicic acid, aluminosilicate, alumina, aluminum hydroxide, magnesium tertiary phosphate, magnesium carbonate, and synthetic resins, alone or in a mixture of two or more (generally in amounts of 10 to 90% by weight based on the total weight of the composition, particularly 20 to 60% by weight in the case of toothpaste). Examples of the humectant include sorbitol, glycerin, propylene glycol, 1,3-butylene glycol, polyethylene glycol, xylitol, maltitol, and lactitol, alone or in admixture of two or more (generally in amounts of 5 to 85% by weight based on the total weight of the composition). Examples of the binder include sodium carboxymethyl cellulose, carrageenan, sodium aliginate, polyacrylic acid and salts thereof, gums, polyvinyl alcohol, and hydroxyethyl cellulose, alone or in admixture of two or more (generally in amounts of 0.3 to 5% by weight based on the total weight of the composition).

Also included are sweeteners such as saccharin sodium, stevioside, neohesperidyl dihydrochalcone, taumatin, glycyrrhizin, perillartine, etc.; preservatives such as p-hydroxybenzoates, sodium benzoate, etc.; and other components. When p-hydroxybenzoates are used as preservatives, their amount should preferably be 0.2% by weight or less because more than 0.3% of p-hydroxybenzoates provides a stimulating taste, resulting in oral compositions of less pleasant feel.

Other forms of oral compositions may be prepared in a conventional manner using selected components for a particular form of composition.

The thus obtained compositions is received in suitable containers such as aluminum tubes, laminate tubes in which aluminum foil is plastic laminated on either surface, plastic tubes, bottles, aerosol containers, and the like before it is ready for use.

The composition of the invention should preferably be adjusted in pH to 5 to 6.5. Outside this range, the lowering in the activity of triclosan may not be prevented satisfactorily.

The oral composition of the invention is formulated with water-soluble tin salts, so that the lowering in activity of triclosan by an alkyl sulfate can be prevented and, thus, good plaque formation-inhibiting effect based on the intense germicidal action of triclosan is attained. The composition of the invention is effective in preventing paradentosis.

EXAMPLES

The invention is more particularly described by way of examples, which should not be construed as limiting the invention.

EXAMPLE 1

A test solution having the following formulation was prepared. 0.3 ml of *Escherichia coli* suspension with $1.0 \times 10^8$ CFU/ml was added to 2.7 ml of the test solution, followed by sterilization reaction on a water bath at 35° C. for one minute. After completion of the reaction, the test solution was diluted with a SCDLP medium (made by Nippon Pharm. Co., Ltd.) and a given amount was cultivated overnight on a SCDLP agar plate (made by Nippon Pharm. Co., Ltd.) to determine the number of viable bacteria. The evaluation was made according to the following standard. The results are shown in Table 1.

| Formulation of test composition | |
|---|---|
| Propylene glycol | 4.0% |
| D-sorbitol | 20.0 |
| Triclosan | 0.05 |
| Surface active agent (indicated in Table 1) | 0.5 |
| Tin compound (indicated in Table 1) | 0.1 |
| Phosphate buffer solution (10 mM) | balance |
| Total | 100.0% |

TABLE 1

| No. | Triclosan | Surface active agent | Tin compound | Log CFU | pH |
|---|---|---|---|---|---|
| 1 | — | — | — | 8.2 | 5.5 |
| 2 | — | sodium lauryl sulfate | — | 8.0 | 5.5 |
| 3 | ◯ | sodium lauryl sulfate | — | 8.0 | 5.5 |
| 4 | — | sodium lauryl sulfate | stannous fluoride | 8.0 | 5.5 |
| 5 | — | sodium lauryl sulfate | stannous pyrophosphate | 8.0 | 5.5 |
| 6 | ◯ | sodium lauryl sulfate | stannous fluoride | 4.6 | 5.5 |
| 7 | ◯ | sodium lauryl sulfate | stannous pyrophosphate | 6.9 | 5.5 |
| 8 | ◯ | Na lauryl ether sulfate | — | 8.0 | 5.5 |
| 9 | ◯ | Na lauryl ether sulfate | stannous fluoride | 7.8 | 5.5 |

As will be apparent from the results of Table 1, when triclosan was used in combination with the alkyl sulfate surface active agent, no germicidal activity was recognized (No. 3). However, when a water-soluble tin compound such as stannous fluoride is added to the combination of the triclosan and the alkyl sulfate surface active agent, the lowering in the germicidal activity of triclosan in the alkyl sulfate surface active agent can be suppressed (No. 6). This effect was not recognized when the water-insoluble tin compound (stannous pyrophosphate) was used in combination.

EXAMPLE 2

Toothpaste

| Aluminum hydroxide | 45.0% |
|---|---|
| Gelling silica | 2.0 |
| Sorbitol | 25.0 |
| Sodium carboxymethyl cellulose | 1.0 |
| Sucrose monopalmitate | 1.0 |
| Sodium lauryl sulfate | 1.5 |
| Sodium saccharin | 0.2 |
| Ethanol | 0.1 |
| Sodium benzoate | 0.1 |
| Gelatin | 0.1 |
| Triclosan | 0.3 |
| Stannous fluoride | 0.2 |
| Sodium phytate | 0.5 |
| Flavor | 1.0 |
| Water | Balance |
| Total | 100.0% |

EXAMPLE 3

Toothpaste

| Precipitated silica | 25.0% |
|---|---|
| Sorbitol | 25.0 |
| Glycerin | 25.0 |

-continued

| | |
|---|---|
| Polyvinyl pyrrolidone | 1.0 |
| Sodium polyacrylate | 1.0 |
| Lauryl polyglycerin ester | 1.0 |
| Sodium lauryl sulfate | 1.0 |
| Sodium saccharin | 0.2 |
| Ethyl p-oxybenzoate | 0.1 |
| Sodium hydroxide | 0.1 |
| Triclosan | 0.2 |
| Stannous fluoride | 0.4 |
| Flavor | 1.0 |
| Water | Balance |
| Total | 100.0% |

EXAMPLE 4

Toothpaste

| | |
|---|---|
| Precipitated silica | 25.0 |
| Gelling silica | 2.0 |
| Sorbitol | 20.0 |
| Propylene glycol | 2.5 |
| Sodium carboxymethyl cellulose | 1.0 |
| Lauryl diethanol amide | 1.0 |
| Sodium lauryl sulfate | 1.5 |
| Sodium lauroyl sarcosinate | 0.3 |
| Sodium saccharin | 0.1 |
| Ethyl p-oxybenzoate | 0.1 |
| Triclosan | 0.05 |
| Stannous gluconate | 0.3 |
| Gelatin | 0.2 |
| Flavor | 0.8 |
| Water | Balance |
| Total | 100.0% |

EXAMPLE 5

Oral paste

| | |
|---|---|
| Cetanol | 10.0 |
| Squalane | 20.0 |
| Gelling silica | 5.0 |
| Polyoxyethylene (40 mol) hydrogenated castor oil | 0.1 |
| Sorbitan monooleate | 1.0 |
| Sodium lauryl sulfate | 0.2 |
| Glycyrrhetinic acid | 0.1 |
| Sodium saccharin | 0.6 |
| Triclosan | 0.3 |
| Stannous fluoride | 0.1 |
| Flavor | 0.6 |
| Water | Balance |
| Total | 100.0% |

EXAMPLE 6

Oral paste

| | |
|---|---|
| Liquid paraffin | 15.0 |
| Cetanol | 10.0 |
| Glycerin | 20.0 |
| Sorbitan monooleate | 0.6 |
| Polyoxyethylene (40 mol) sorbitan monostearate | 5.0 |
| Sodium lauryl sulfate | 0.1 |
| Sodium saccharin | 0.5 |
| Benzetonium chloride | 0.1 |
| Triclosan | 0.2 |
| Stannous fluoride | 0.05 |
| Flavor | 0.5 |
| Water | Balance |
| Total | 100.0% |

EXAMPLE 7

Mouthwash

| | |
|---|---|
| Sorbitol | 10.0% |
| Ethanol | 5.0 |
| Polyoxyethylene (60 mol) hydrogenated castor oil | 0.1 |
| Sucrose monopalmitate | 0.2 |
| Sodium lauryl sulfate | 0.05 |
| Sodium saccharin | 0.2 |
| Sodium hydroxide | 0.05 |
| Triclosan | 0.05 |
| Stannous fluoride | 0.15 |
| Flavor | 0.6 |
| Water | Balance |
| Total | 100.0% |

EXAMPLE 8

Troche

| | |
|---|---|
| Lactose | 97.0% |
| Polyoxyethylene (60 mol) monostearate | 0.2 |
| Sodium lauryl sulfate | 0.05 |
| Chlorhexidine (gluconic acid salt) | 0.02 |
| Stevia extract | 0.2 |
| Gelatin | 0.4 |
| Triclosan | 0.2 |
| Stannous gluconate | 0.1 |
| Flavor | 0.02 |
| Hydroxyethyl cellulose | Balance |
| Total | 100.0% |

We claim:
1. An oral composition consisting essentially of:
    0.001 to 1.0% by weight of the total weight of the oral composition of triclosan;
    0.01 to 10% by weight of the total weight of the oral composition of an alkyl sulfate;
    0.01 to 10% by weight of the total weight of the oral composition of a water-soluble tin salt selected from the group consisting of stannous fluoride, stannous chloride, stannous fluoride chloride, stannous acetate, stannous sulfate, stannous tartrate, stannous gluconate and stannous citrate; and
    one or more optional effective ingredients in an amount not impeding the germicidal effect of triclosan selected from the group consisting of abrasives, binders, humectants and flavors.
2. The oral composition according to claim 1, wherein the alkyl sulfate has 8 to 18 carbon atoms in the alkyl group.
3. The oral composition according to claim 1, wherein said composition is in the form of a member selected from the group consisting of toothpaste, toothpowder, mouthwash, gingiva-massage cream, ointment, troche, and chewing gum.
4. The oral composition according to claim 1, wherein the triclosan is present in an amount of from 0.01 to 0.05% by weight of the total weight of the oral composition,
    the alkyl sulfate is present in the amount of from 0.1 to 5% by weight of the total weight of the oral composition, and
    the water-soluble tin salt is present in the amount of 0.1 to 2% by weight of the total weight of the oral composition.

5. The oral composition according to claim 1, wherein the alkyl sulfate has 10 to 14 carbon atoms in the alkyl group.

6. The oral composition according to claim 1, wherein the alkyl sulfate is selected from the group consisting of sodium lauryl sulfate and sodium myristyl sulfate.

7. The oral composition according to claim 1, wherein the water-soluble tin salt is selected from the group consisting of stannous fluoride, stannous chloride and stannous gluconate.

8. The oral composition according to claim 1, wherein the pH is from 5 to 6.5.

9. The oral composition according to claim 1, wherein the alkyl sulfate is sodium lauryl sulfate and the water-soluble tin salt is stannous fluoride.

10. The oral composition according to claim 1, wherein the water-soluble tin salt is stannous fluoride and the oral composition is in the form of a toothpaste.

* * * * *

UNITED STATES PATENT AND TRADEMARK OFFICE
CERTIFICATE OF CORRECTION

PATENT NO. : 5,348,733

DATED : September 20, 1994

INVENTOR(S) : Seiji MORISHIMA, Miwako OKA and Yoji YAMAZAKI

It is certified that error appears in the above-identified patent and that said Letters Patent is hereby corrected as shown below:

TITLE PAGE

Changing the arrangement of the inventor's name from "Yamazaki Yoji" to --Yoji Yamazaki--.

Signed and Sealed this

Fifteenth Day of November, 1994

*Attest:*

BRUCE LEHMAN

*Attesting Officer*  Commissioner of Patents and Trademarks